US012029580B2

(12) United States Patent
Koch et al.

(10) Patent No.: US 12,029,580 B2
(45) Date of Patent: Jul. 9, 2024

(54) PROVIDING A PARAMETER WHICH INDICATES A LOSS OF CONSCIOUSNESS OF A PATIENT UNDER ANESTHESIA

(71) Applicant: Covidien LP, Mansfield, MA (US)

(72) Inventors: Susanne Koch, Berlin (DE); Claudia Spies, Berlin (DE)

(73) Assignee: COVIDIEN LP, Mansfield, MA (US)

( * ) Notice: Subject to any disclaimer, the term of this patent is extended or adjusted under 35 U.S.C. 154(b) by 899 days.

(21) Appl. No.: 17/049,479

(22) PCT Filed: Apr. 26, 2019

(86) PCT No.: PCT/EP2019/060788
§ 371 (c)(1),
(2) Date: Oct. 21, 2020

(87) PCT Pub. No.: WO2019/207130
PCT Pub. Date: Oct. 31, 2019

(65) Prior Publication Data
US 2021/0244353 A1 Aug. 12, 2021

(30) Foreign Application Priority Data
Apr. 27, 2018 (DE) .......................... 102018110275.5

(51) Int. Cl.
*A61B 5/00* (2006.01)
*A61B 5/291* (2021.01)
(Continued)

(52) U.S. Cl.
CPC ............ *A61B 5/4821* (2013.01); *A61B 5/291* (2021.01); *A61B 5/372* (2021.01); *A61B 5/384* (2021.01); *A61B 5/7225* (2013.01)

(58) Field of Classification Search
CPC ....... A61B 5/4821; A61B 5/291; A61B 5/372; A61B 5/384; A61B 5/7225; A61B 5/374; G16H 50/30
See application file for complete search history.

(56) References Cited

U.S. PATENT DOCUMENTS 5,010,891 A * 4/1991 Chamoun ................ A61B 5/16
600/544
5,813,993 A * 9/1998 Kaplan ................ A61B 5/7203
600/26
(Continued)

FOREIGN PATENT DOCUMENTS

CN 101449974 A 6/2009
CN 103153178 A 6/2013
(Continued)

OTHER PUBLICATIONS

Hayashi et al., "Electroencephalographic changes in the late cardiopulmonary bypass period are not reflected in the bispectral index". Clinical Neurophysiology. Elsevier Science. Vol. 121, No. 8, Aug. 2010, pp. 1198-1204.
(Continued)

*Primary Examiner* — May A Abouelela
(74) *Attorney, Agent, or Firm* — Fletcher Yoder, P.C.

(57) ABSTRACT

The invention relates to a method and a device for providing a parameter which indicates a loss of consciousness of a patient under anesthesia. The method has the steps of detecting (301) at least one EEG signal on the head of the patient; continuously determining (302) the spectral cut-off frequency in a current timeframe of the EEG signal; determining (303) the curve of the spectral cut-off frequency of the EEG signal in a period of time which begins before an anesthesia-inducing medication is administered and ends after the anesthesia-induced loss of consciousness is initiated; determining (304) the absolute minimum of the spec- (Continued)

tral cut-off frequency in the period of time, wherein a negative peak of the spectral cut-off frequency lies in the absolute minimum, and providing (305) information regarding at which point in time the absolute minimum was reached as a parameter for an indicative notification of the loss of consciousness of the patient.

21 Claims, 5 Drawing Sheets

(51) Int. Cl.
    *A61B 5/372*     (2021.01)
    *A61B 5/384*     (2021.01)

(56) References Cited

U.S. PATENT DOCUMENTS

| | | | |
|---|---|---|---|
| 5,846,208 A | 12/1998 | Pichlmayr et al. | |
| 6,011,990 A | 1/2000 | Schultz et al. | |
| 6,493,576 B1* | 12/2002 | Dankwart-Eder | A61B 5/38 600/544 |
| 6,934,579 B2* | 8/2005 | Mantzaridis | A61B 5/1106 600/544 |
| RE41,291 E* | 4/2010 | Viertio-Oja | A61M 16/01 600/546 |
| 7,774,052 B2 | 8/2010 | Burton et al. | |
| 7,805,187 B2 | 9/2010 | Sarkarla et al. | |
| 7,920,914 B2 | 4/2011 | Shieh et al. | |
| 8,352,023 B2* | 1/2013 | John | A61B 5/021 600/545 |
| 8,538,705 B2 | 9/2013 | Greenwald | |
| 8,838,226 B2 | 9/2014 | Bibian et al. | |
| 9,474,452 B2 | 10/2016 | Kochs et al. | |
| 10,542,905 B2* | 1/2020 | Mhuircheartaigh | A61B 5/4839 |
| 2003/0023183 A1 | 1/2003 | Williams | |
| 2009/0275853 A1 | 11/2009 | Sarkela | |
| 2013/0197339 A1* | 8/2013 | Bardakjian | A61B 5/726 600/383 |
| 2014/0081094 A1* | 3/2014 | Jordan | A61B 5/725 600/383 |
| 2014/0187973 A1 | 7/2014 | Brown et al. | |
| 2016/0045128 A1* | 2/2016 | Sitt | A61B 5/316 600/475 |
| 2016/0228705 A1 | 8/2016 | Crowder et al. | |
| 2016/0324446 A1* | 11/2016 | Prerau | A61B 5/374 |
| 2016/0331307 A1* | 11/2016 | Purdon | A61B 5/316 |
| 2017/0231556 A1* | 8/2017 | Purdon | A61B 5/4821 600/544 |
| 2019/0143040 A1* | 5/2019 | Guerrini | G16H 20/17 604/503 |

FOREIGN PATENT DOCUMENTS

| | | |
|---|---|---|
| CN | 104644166 A | 5/2015 |
| CN | 204542061 U | 8/2015 |
| KR | 10-1893596 | 8/2018 |
| WO | 2014/059418 | 4/2014 |

OTHER PUBLICATIONS

Gilron et al., "40 Hz auditory steady-state response and EEG spectral edge frequency during sufentanil anaesthesia", Can J. Anaesth, vol. 45, No. 2, Feb. 1998, pp. 115-121.

Gerritzen et al., "Progress report validation of parameters to examine unconsciousness", Livestock Research Report, May 2014, 38 pp.

Sebel et al., "A Multicenter Study of Bispectral Electroencephalogram Analysis for Monitoring Anesthetic Effect", Anesthesia & Analgesia, vol. 84, No. 4, Apr. 1997, pp. 891-899.

Purdon et al., "Electroencephalogram signatures of loss and recovery of consciousness from propofol", Proc Natl Acad Sci USA, Mar. 4, 2013, pp. 1142-1151.

International Search Report and Written Opinion, and English translation thereof, from International Application No. PCT/EP2019/060788, dated Jul. 2, 2019, 20 pp.

International Preliminary Report on Patentability, and translation thereof, from International Application No. PCT/EP2019/060788, dated Oct. 27, 2020, 15 pp.

Loskota, "Intraoperative EEG monitoring", Seminars in Anesthesia, Perioperative Medicine and Pain, vol. 24, Dec. 2005, pp. 176-185.

Katoh, Influence of Age on Hypnotic Requirement, Bispectral Index, and 95% Spectral Edge Frequency Associated with Sedation Induced by Sevoflurane, Anesthesiology, vol. 92, Issue 1, Jan. 2000, pp. 55-61.

"SedLine® Sedation Monitor Quick Reference Guide," Masimo, retrieved from https://www.masimo.com/siteassets/us/documents/pdf/plm-10355c_quick_reference_guide_sedline_english.pdf on Feb. 3, 2021, 7 pp.

Schwender, "Spectral edge frequency of the electroencephalogram to monitor "depth" of anaesthesia with isoflurane or propofol," British Journal of Anaesthesia, vol. 77, Aug. 1996, pp. 179-184.

Colombo, "The Spectral Exponent of the Resting EEG Indexes the Presence of Consciousness during Unresponsiveness Induced by Propofol, Xenon, and Ketamine," NeuroImage, Apr. 2019, 26 pp.

CN Office Action for Chinese Application No. 201980027777.8 mailed Feb. 1, 2024.

\* cited by examiner

PROVIDING A PARAMETER WHICH INDICATES A LOSS OF CONSCIOUSNESS OF A PATIENT UNDER ANESTHESIA

This application is a U.S. National Stage entry under 35 U.S.C. § 371 of International Application No. PCT/EP2019/060788, filed Apr. 26, 2019, which claims priority to German Patent Application No. DE 10 2018 110 275, filed on Apr. 27, 2018.

The invention relates to a method and to a device for providing a parameter, which indicates a loss of consciousness in a patient under anesthesia.

Deducing cerebral activity by means of surface electrodes as an electroencephalogram (EEG) has been known since the 1930s. Regularly monitoring the depth of anesthesia by means of frontal EEG deduction has been known since the 1990s, in which EEG data analysis is restricted to calculating an index that is calculated by means of a stored algorithm and is intended to provide the anesthetist with a simple estimation of the depth of anesthesia; see Sebel P S, Lang E, Rampil I J, White P F, Cork R, Joplin M. Smith N T, Glass P S A, Manberg P: "A Multicenter Study of Bispectral Electroencephalogram Analysis for Monitoring Anesthetic Effect," Anesth Analg 1997; 84 (4): 891-899.

During their day-to-day work, it is advantageous for an anesthetist to be able to accurately determine the occurrence of the loss of consciousness (LOC) when anesthetic has been administered, since (1) too early intubation with the patient's subsequent perception of pain can be avoided and (2) too late intubation, which carries the risk of complications such as aspiration as a result of the deep state of anesthesia together with the loss of protective reflexes, can be avoided as a result. The above-mentioned EEG index shows a drop over the point in time when consciousness is lost (LOC). Therefore, the exact point in time when consciousness is lost can, however, not be determined.

The object of the present invention is to provide a method and a device, which automatedly provide information that allow an anesthetist to determine more precisely the precise determination of the occurrence of the loss of consciousness of a patient when anesthetic has been administered.

This object is achieved by a method having the features of claim 1 and by a device having the features of claim 12. Embodiments of the invention are indicated in the dependent claims.

In a first aspect, the invention subsequently provides a method for providing a parameter, which indicates a loss of consciousness in a patient under anesthesia. According to the method according to the invention, at least one EEG signal is recorded on the patient's head. Furthermore, the spectral cutoff frequency is continuously determined in a current timeframe of the EEG signal. In this case, the spectral cutoff frequency is defined in that it indicates the frequency at which 95% of the overall power is included in the power spectrum. In the power spectrum, the square amplitude is plotted against the frequency. It reflects the particular proportion of the individual frequency regions of the overall power proportion of the raw signal. The spectral cutoff frequency is therefore the frequency below which a specific proportion of the energy of the overall spectrum lies. According to the invention, a proportion of 95% is taken into consideration in this case.

The timeframe under consideration takes into consideration the EEG signal in a period of time that reaches back from the current time by a defined length of time, for example the EEG signal of the last minute or the last 30 seconds or the last 20 seconds. This is a timeframe that migrates over time. The spectral cutoff frequency is determined by means of a spectral analysis in this case. In particular, a discrete Fourier transform is carried out, for example a Fast Fourier Transform (FFT). The timeframe under consideration indicates the timeframe that forms the basis of the spectral analysis in this case.

According to the method according to the invention, the response of the spectral cutoff frequency of the EEG signal is furthermore determined in a period of time that begins before the anesthetic is administered and before the occurrence of an anesthetic-induced loss of consciousness in the patient and ends after the occurrence of the anesthetic-induced loss of consciousness. The absolute minimum of the spectral cutoff frequency in the period of time under consideration is determined, wherein a negative peak of the spectral cutoff frequency is present in the absolute minimum and information relating to the point in time at which the absolute minimum has been reached is provided or output as a parameter for the indicative indication of a loss of consciousness in the patient.

It is pointed out here that the length of said period of time is not necessarily predefined. For example, the period of time may end as soon as the presence of an absolute minimum has been determined.

The invention relates to the surprising knowledge, which is backed up by a study, that the point LOC of the loss of consciousness is accompanied by a brief drop in the spectral cutoff frequency. It was identified that the spectral cutoff frequency briefly drops at the exact point when consciousness is lost, and then subsequently re-increases. In this case, a significant negative peak in the spectral cutoff frequency forms, which is evaluated and the absolute minimum of which is determined. The values for the spectral cutoff frequency drop before the absolute minimum and re-increase behind the absolute minimum. As a result, the absolute minimum can be clearly determined. The brief drop in the spectral cutoff frequency at the point when consciousness is lost and the re-increase therein typically takes place over a period of approximately 1 to 3 minutes, in particular over a period of approximately 2 minutes.

By determining the point in time of the negative peak, i.e. of the absolute minimum of the spectral cutoff frequency in the period of time under consideration, a parameter can therefore be provided that indicatively indicates a loss of consciousness in a patient when anesthetic has been administered and can be taken into consideration by the anesthetist together with additional parameters, if necessary. This allows for improved anesthesia management.

It is pointed out that, in the period of time under consideration, the absolute minimum is determined and the point at which it occurs is given as a parameter. Local minima may also occur, in particular during the drop in the signal, which, however, have significantly higher minimum values than the absolute minimum that indicates the negative peak in the spectral cutoff frequency. The negative peak that contains the absolute minimum is significantly greater than any potential local minima both in terms of its width and its depth, and is therefore easy to detect.

According to the invention, a frontal EEG signal is preferably picked up, i.e. a frontal deduction is carried out, in which the EEG signal is measured at at least two electrodes that are arranged in different places on the patient's forehead. In this case, a plurality of frontal EEG signals may be picked up, which are averaged before the spectral cutoff frequency is determined. In the 10-20 system that is typically used, signals are deduced from electrodes, for example, which are positioned in positions F7, F8, Fp1, Fp2 and Fpz.

A bipolar deduction (difference between two active electrodes) or a unipolar deduction (difference between a plurality of active electrodes against a common reference) can be carried out.

One embodiment of the invention provides that the spectral cutoff frequency is continuously determined by being re-determined at least every 30 seconds, in particular at least every 10 seconds, in particular at least every 2 seconds. It is clear here that the more often the spectral cutoff frequency is determined, the more accurately the point in time of the minimum of the spectral cutoff frequency can be determined.

Another embodiment of the invention provides that the information relating to the point in time at which the absolute minimum has been reached is provided as soon as said minimum has been determined. As soon as the presence of an absolute minimum can be reliably determined, the point in time at which the absolute minimum has been reached is output as a parameter. Since this information is important for the anesthetist as an indication of the occurrence of the loss of consciousness, the information is provided as quickly as possible.

In order to analyze whether the spectral cutoff frequency comprises an absolute minimum, data analysis and curve analysis methods known per se can be used. For example, the information relating to the point in time at which the minimum has been reached can be provided if the spectral cutoff frequency has fallen below a value of 10 hertz, in particular below a value of 9 hertz, and re-increases. It has become apparent that local minima in the response of the spectral cutoff frequency typically lie above this frequency and therefore a drop in the response of the spectral cutoff frequency below a value of 10 hertz or 9 hertz (or even up to 8 hertz) indicates the presence of the absolute minimum.

An alternative evaluation method provides that the information relating to the point in time at which the minimum has been reached is provided if, for a defined number of measured values, the measured value for the spectral cutoff frequency is greater than the previous measured value. The number of measured values that are established as an indication that the spectral cutoff frequency has re-increased and therefore that the absolute minimum has been reached is naturally dependent on how often the spectral cutoff frequency is determined.

Another embodiment provides that the spectral cutoff frequency of the EEG signal is determined after said signal has been filtered through a bandpass filter. The bandpass filter is designed such that it only allows signals in the frequency range of from 0.5-40 Hz to pass through, for example.

One embodiment of the invention provides that the spectral cutoff frequency is ascertained by means of a spectral analysis, a concurrent timeframe of the EEG signal being evaluated in each case. The spectral analysis is carried out by means of an FFT algorithm, for example. However, there exist other possible ways of spectrally decomposing the EEG signal, which can alternatively be used, for example the discrete cosine transform, discrete wavelet transform or signal decomposing by means of a bandpass filter bank.

The method according to the invention is automatedly carried out, in particular by a computer program. The computer program contains program codes for carrying out the method according to claim 1 when the computer program is executed on a computer.

In another aspect of the invention, the invention relates to a device for providing a parameter, which indicates a loss of consciousness in a patient under anesthesia. The device comprises:
- means designed to record at least one EEG signal on the patient's head,
- means designed to continuously determine the spectral cutoff frequency in a current timeframe of the EEG signal, wherein the spectral cutoff frequency indicates the frequency at which 95% of the overall power is included in the power spectrum,
- means designed to determine the response of the spectral cutoff frequency of the EEG signal in a period of time that begins before an anesthesia-inducing medicine is administered and finishes after the occurrence of the anesthesia-induced loss of consciousness,
- means designed to determine the absolute minimum of the spectral cutoff frequency in the time period, wherein a negative peak of the spectral cutoff frequency is present in the absolute minimum, and
- means designed to provide information relating to the point in time at which the absolute minimum has been reached as a parameter for the indicative indication of a loss of consciousness in the patient.

Said means can be formed by a microprocessor in conjunction with a program code that the microprocessor executes.

In another aspect, the invention relates to an EEG anesthesia monitor comprising a device according to claim 12. The device according to the invention is therefore integrated in an EEG anesthesia monitor, in which said monitor is intended and designed to analyze and present EEG data in real time.

The invention will be explained in more detail in the following with reference to the figures in the drawings and on the basis of several embodiments, in which.

Figure 1:
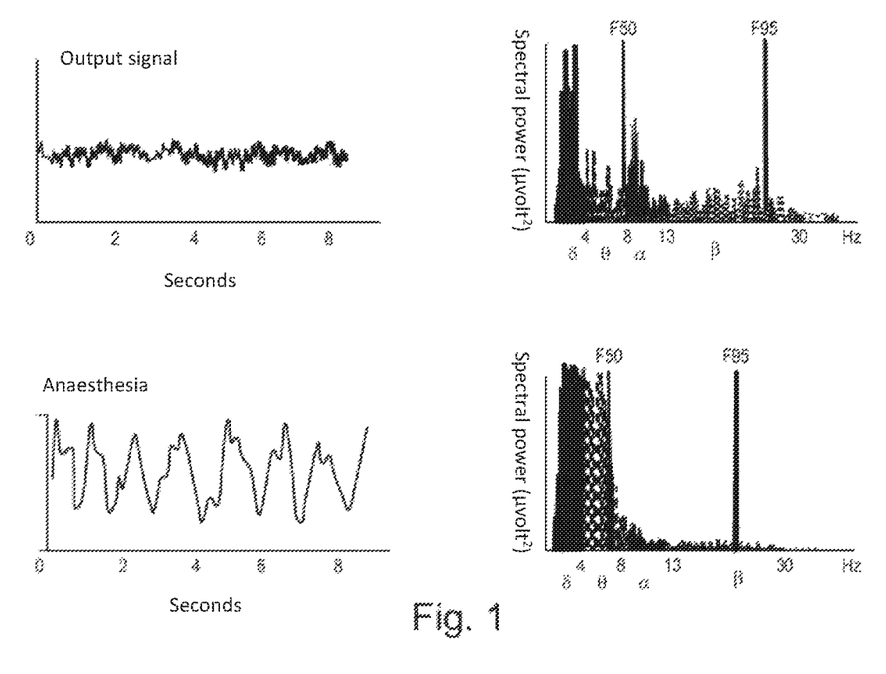
FIG. 1 shows, by way of example, EEG signals in the awake state and after an anesthesia-induced loss of consciousness both as a time-dependent signal and in the power spectrum.
Figure 2:
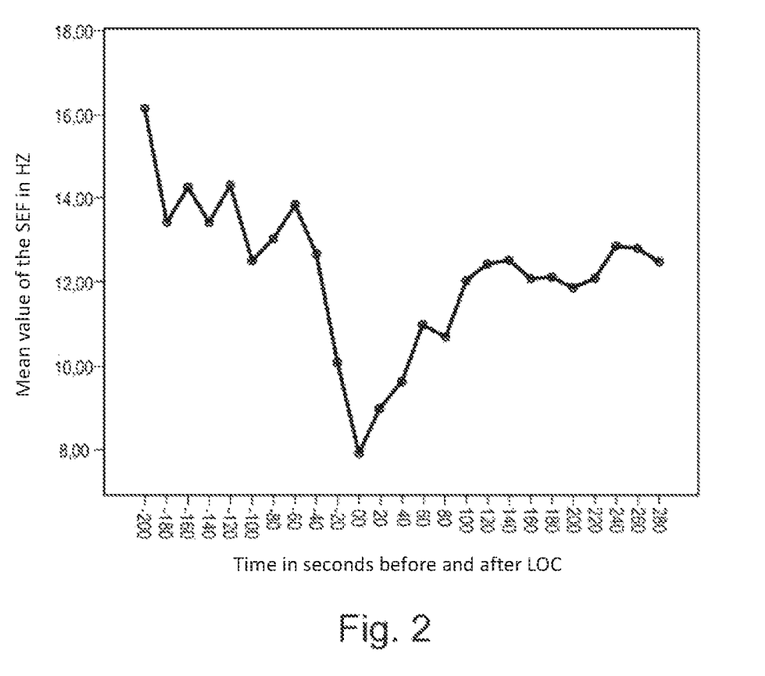
FIG. 2 shows, by way of example, the temporal course of the spectral cutoff frequency in a period of time that begins before the occurrence of an anesthesia-induced loss of consciousness in a patient and ends after the occurrence of the anesthesia-induced loss of consciousness.

The relationship that is identified first according to the present invention between the time course of the spectral cutoff frequency and the occurrence of the loss of consciousness when anesthetic has been administered will firstly be explained on the basis of FIGS. 1 and 2, which relationship has been proven by means of a study.

In order to explain the background of the invention, FIG. 1 shows in the upper illustration (output signal) an EEG signal as occurs in a patient that is awake. The signal is depicted both as a time signal (left) and as a power spectrum (right) following a spectral analysis. In the power spectrum, the power (the square amplitude) is plotted in db against the frequency in Hz. The power spectrum displays the relevant proportion of the overall power proportion of the raw signal that the individual frequency ranges make up. The spectral cutoff frequency SEF is likewise shown. This is defined as the frequency below which a proportion of 95% of the energy of the overall spectrum lies. The median frequency F50 is also depicted, but this does not matter in the present case.

The bottom representation ("anesthesia") in FIG. 1 shows an EEG signal under anesthesia. It is evident that the spectral cutoff frequency SEF is shifted to the left with respect to the value in a patient that is awake.

The spectral cutoff frequency (SEF) therefore provides information regarding how awake a patient is. Since in the awake state the EEG signal contains higher frequencies, high values occur for the spectral cutoff frequency. In the asleep state or under anesthesia, slow frequencies dominate in the EEG such that lower values occur for the spectral cutoff frequency.

The processes during the introduction of an anesthetic are now observed. When introducing an anesthetic, the patient is initially awake. High SEF values of approximately 17-20 Hz occur. The patient passes into a deep loss of consciousness under anesthesia. Purdon P L, Pierce E T, Mukamel E A, Prerau M J, Walsh J L, Wong K F K, Salazar-Gomez A F, Harrell P G, Sampson A L, Cinemser A, Ching S, Kopell N J, Tavares-SToeckel C, Habeeb K, Merhar R, Brown E.: "Electroencephalogram signatures of loss and recovery of consciousness from propofol," PNAS 2013; 110 (12): E1142-1151 have shown that a deep loss of consciousness induced by GABA-activating anesthetics leads to a frontal alpha-band activation. As a result, relatively higher SEF values of 12-17 Hz are also shown during surgery amid a deep loss of consciousness.

In the present case, a prospective observational study was able to show that there is a very brief drop in the SEF value at precisely the point of the anesthetic-induced loss of consciousness, which is associated with a subsequent re-increase. The minimum of the resultant negative peak here indicates the point in time of the anesthesia-induced loss of consciousness.

The study was carried out on a group of a total of 37 older patients, in which the anesthetic was introduced with one of the most frequently used anesthetics, specifically Propofol. It may be assumed that, in younger adults, there is an even more significant drop in the spectral cutoff frequency at the point of the anesthetic-induced loss of consciousness.

Figure 5:
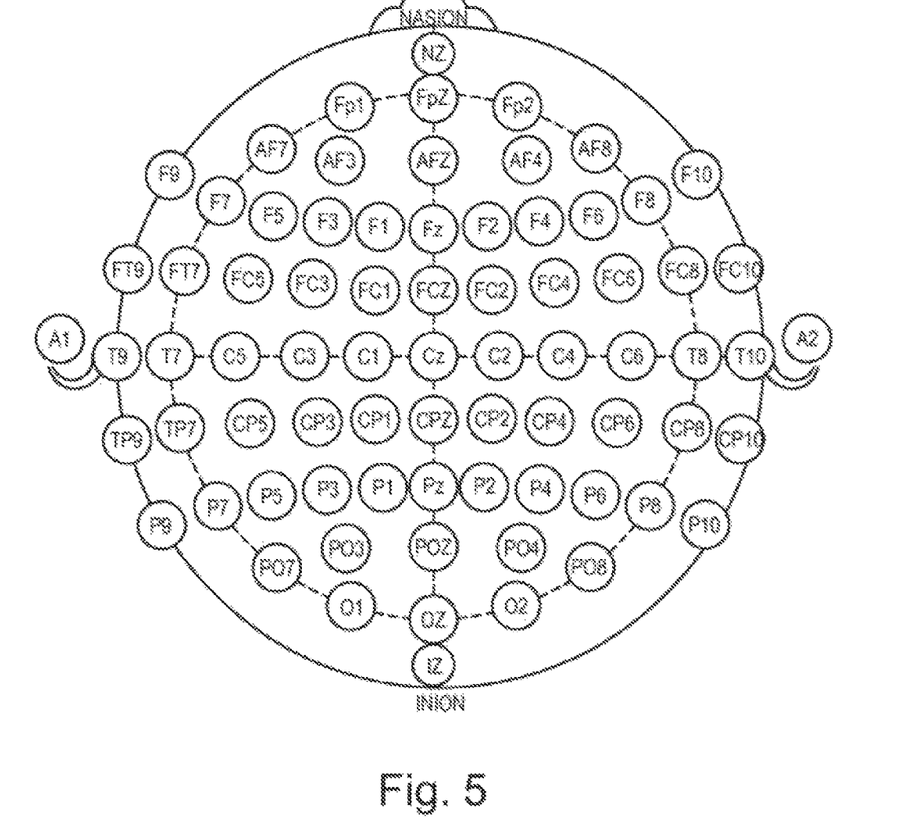
FIG. 5 shows positioning points for EEG electrodes according to the 10-20 system.

The measurements were carried out as follows:

a) EEG Deduction:

In the perioperative EEG determination, the EEG electrodes were affixed to the patient while they were still awake before the first medication was administered by the anesthetist. For this purpose, the forehead and the temples were thoroughly disinfected and freed of skin oils. This measure improved the conductivity of the skin and therefore guaranteed an interference-free deduction of the EEG signals. The ready-made EEG self-adhesive electrodes by Masimo (4248RD SEDLine Sensor, Single Patient Use, Non-Sterile) were then affixed to the forehead on the prepared skin areas, in which the EEG electrodes each rest on the positions F7, F8, FP1 and FP2 according to the 10/20 system, with Pfz as the reference electrode. The corresponding positions are shown in FIG. 5. The impedance of the individual electrodes was below 5 kD and the sampling rate was 250 Hz during the deduction. A bandpass filter was preset to 0.5-40 Hz.

After connecting the self-adhesive electrodes to an EEG-based brain function monitor (the "SEDLine Monitor" by Masimo Corporation, Irvine, California), the deduction and recording of a continuous 4-channel EEG was begun. The patients were still awake at this point, and therefore the first values of the deduction corresponded to a baseline activity.

In order to determine specific points in time during the EEG deduction, "Event Markers" were manually entered in the EEG during the EEG recording. The administration of the medicine was initiated by the anesthetist in the process. This point in time was noted as the event marker "Start Anesthesia." All patients were given the medication Propofol intravenously in order to initiate the anesthesia. The state of consciousness of the patient was continuously checked by means of the eyelid reflex, in the event of no eyelid reflex a loss of consciousness was assumed and the event marker "loss of consciousness" was set. This procedure allows for the data to be evaluated exactly to the second.

b) EEG Evaluation

The following data were recorded by the SEDLine monitor: the spectral cutoff frequency (SEF), the anesthesia index (PSI), the artifact level and the electromyographic activity. These EEG data were manually exported from the SEDLine monitor and displayed in numerical format on the computer in Excel tables.

By means of the recording rate of the SEDLine of 30 values per minute, all measured values were provided every two seconds. For each patient, a check was first made to see whether the "baseline," "start anesthesia" and "loss of consciousness" points in time tested had been fully drawn and were free from artifacts. For this purpose, both the artifact level calculated by the instrument and the EMG artifacts likewise drawn were inspected. Usable data records were divided into timeframes of 20 seconds each for "loss of consciousness." During each timeframe that stretched from 200 seconds before "loss of consciousness" to 200 seconds after "loss of consciousness," the artifact-free spectral cutoff frequency of each patient was averaged for the right and left cerebral hemisphere.

The power spectrum for determining the spectral cutoff frequency was therefore determined in EEG signal timeframes of 20 seconds, in which an update was made every 2 seconds. The calculation was carried out by means of digital computer-assisted EEG signal processing. The basis for this is the spectral analysis of the raw EEG by means of Fast Fourier Transformation, by means of which the power proportions for each timeframe currently to be analyzed can be calculated.

In order to firstly ascertain whether there is a difference between the examination of the right and left hemisphere, the values before the medication was administered (−200 seconds), at the point in time of the loss of consciousness (0 seconds) and after the introduction (+200 seconds) in all patients having a dominant right hand (n=36) were used to carry out a 2-sided t-test for dependent samples. Since at none of the points in time was there a significant difference (before the medication was administered p=0.26, during a loss of consciousness p=0.940, after introduction p=0.44), the relevant average value was worked with for the right and left cerebral hemisphere in the further course.

All variables were tested for their normal distribution. For this purpose, the histogram and the Q-Q plot were each visually inspected and the data were analyzed by means of the Lilliefors Tests, the Shapiro-Wilk test and the values were analyzed for skewness and kurtosis.

In order to depict the introduction, operation and removal, the times indicated for the event markers of the EEG deduction were evaluated and tested for average values and standard deviations by means of descriptive statistics.

The response of the spectral cutoff frequency was examined in order to determine the occurrence of the anesthesia-induced loss of consciousness in the context of a single-factor one-way ANOVA ("analysis of variance") and the associated post-hoc test.

In order to examine the spectral cutoff frequency in the period of time from 200 seconds before the occurrence of the anesthesia-induced loss of consciousness up to 200 seconds after the occurrence of the anesthesia-induced loss of consciousness for a possible influence of the point in time of the intubation, the start of the intubation was correlated with the points in time from 20 seconds after "loss of consciousness" up to 200 seconds after "loss of consciousness" using the correlation according to Pearson. In order to demonstrate the response without the possible influence of the intubation, the study population was divided into two groups. Patients in which intubation was begun within 200 seconds after "loss of consciousness" represented one group, patients in which intubation was begun after more than 200 seconds represented the other group. These were then examined for equality of variances using the Levene test and then tested for significant differences between groups using a t-test for independent samples. By only presenting those cases in which the intubation was only carried out after the period of time under consideration, the intubation could therefore be eliminated as a possible interference factor.

FIG. 2 shows the average values determined during the study for the spectral cutoff frequency (SEK) as a function of time. In this case, the average value for the spectral cutoff frequency is given in Hz over the point in time of the loss of consciousness during the period of time from 200 seconds before the loss of consciousness up to 280 seconds after the loss of consciousness. The loss of consciousness (LOC) is denoted as "00" on the time axis here.

The following table indicates the numerical values for the diagram in FIG. 2 including the particular standard deviation:

| Point in time in seconds before/after LOC | Average value in Hz | Standard deviation |
| --- | --- | --- |
| −200 | 16.1522 | 6.63732 |
| −180 | 13.4322 | 5.82472 |
| −160 | 14.2643 | 6.29292 |
| −140 | 13.4243 | 6.27143 |
| −120 | 14.3168 | 6.59561 |
| −100 | 12.5081 | 6.12921 |
| −80 | 13.0448 | 5.61589 |
| −60 | 13.8354 | 5.55857 |
| −40 | 12.6829 | 5.85254 |
| −20 | 10.1051 | 4.09247 |
| 00 | 7.9307 | 3.96740 |
| 20 | 9.0013 | 3.71247 |
| 40 | 9.6232 | 3.08994 |
| 60 | 10.9800 | 2.94291 |
| 80 | 10.6930 | 3.24560 |
| 100 | 12.0464 | 2.41244 |
| 120 | 12.4408 | 2.80897 |
| 140 | 12.5120 | 3.03307 |
| 160 | 12.0910 | 2.51989 |
| 180 | 12.1213 | 3.70452 |
| 200 | 11.8718 | 3.60563 |
| 220 | 12.0961 | 3.69842 |
| 240 | 12.8673 | 3.18760 |
| 260 | 12.8035 | 3.35782 |
| 280 | 12.4916 | 3.15537 |
| Overall | 11.8354 | 4.38536 |

A clear negative peak can be seen, which has its minimum at the point in time of the loss of consciousness (point in time "00"). The spectral frequency average drops from values of approximately 12-14 Hz to approximately 8 Hz in this case and then increases to approximately 12-13 Hz. The width of the negative peak is approximately 2 minutes. By determining the minimum of the negative peak, the occurrence of the loss of consciousness can be determined with an accuracy of 20 seconds or even less.

According to the invention, the correlations determined are evaluated electronically or using a computer and are used to determine the response of the spectral cutoff frequency of the EEG signal and to determine the absolute minimum of the spectral cutoff frequency in said response as a parameter for the occurrence of the anesthesia-induced loss of consciousness. The associated program can be integrated in an EEG-based brain function monitor or electroencephalograph as a software tool in this case.

Figure 3:
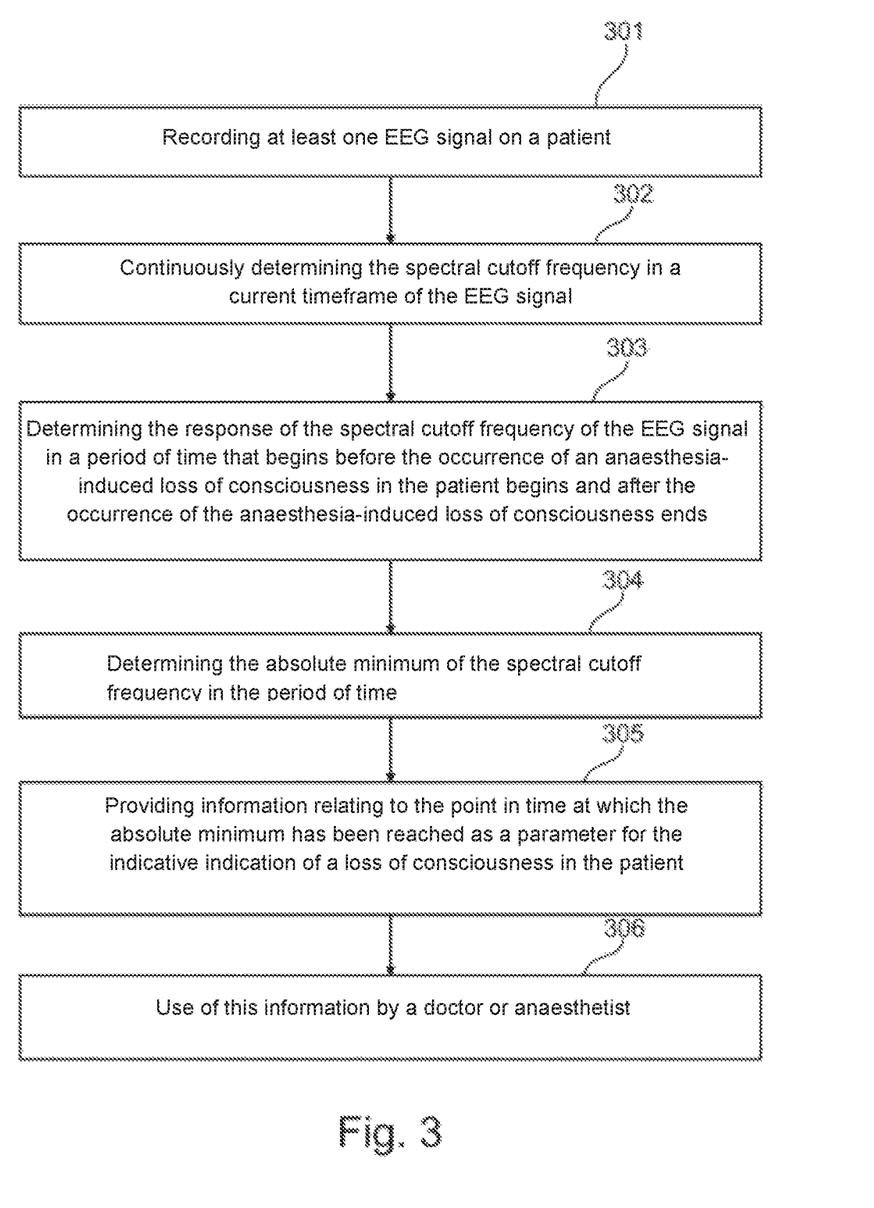
FIG. 3 is a flow diagram of the method according to the invention.

FIG. 3 shows the method for determining a parameter, which indicates a loss of consciousness in a patient under anesthesia. According to step 301, at least one frontal EEG signal is recorded on a patient. For example, four EEG signals are picked up by means of electrodes in the positions F7, F8, FP1 and FP2 according to the 10/20 system, with Fpz as the reference electrode and an average of these signals is given.

According to step 302, the spectral cutoff frequency is continuously determined within a current timeframe of the EEG signal. The determination is carried out continuously, for example in that an up-to-date determination of the spectral frequency is made every 2 seconds or every 5 seconds. The current timeframe has a length of 20 seconds, for example, in which said values are only to be understood by way of example.

In step 303, the response of the spectral cutoff frequency of the EEG signal is evaluated. This is carried out in a period of time that begins before an anesthesia-inducing medication (for example Propofol) is administered and after the occurrence of the anesthesia-induced loss of consciousness ends. In this case, the period of time can or cannot be established with regard to its duration. In the second instance, the period of time ends as soon as the minimum could be determined for the spectral cutoff frequency, for example.

In step 304, the absolute minimum is determined for the spectral cutoff frequency in the period of time under consideration. For example, this can be carried out by evaluating whether or not the spectral cutoff frequency has fallen below a value of 10 hertz, in particular below a value of 9 Hertz, and re-increases. Alternatively or in addition, it is also possible to evaluate whether, for a defined number of measured values, the measured value for the spectral cutoff frequency is greater than the previous measured value. A negative peak in the spectral cutoff frequency is therefore evaluated, in which the absolute minimum of the spectral cutoff frequency lies in the negative tip of the negative peak. Additional data analysis and curve sketching methods can be used to determine the absolute minimum of the spectral cutoff frequency with the greatest possible degree of accuracy.

As soon as the absolute minimum has been determined for the spectral frequency, this information is provided, for example acoustically and/or on the display of an EEG monitor, as a parameter in order to indicatively indicate a loss of consciousness in the patient.

According to step 306, a doctor or an anesthetist can use this information to accurately adapt an intubation to be carried out to the patient's individual state of conscious so as not to carry out the intubation too early or too late. This leads to a greater degree of safety for patients when introducing the anesthetic.

In order to carry out the method, an EEG-based brain function monitor or a computer in general can be used. The method steps for determining and evaluating the spectral cutoff frequency and for determining the absolute minimum of the spectral cutoff frequency are carried out by a program code here, which is executed in a processor. The program code is stored in a memory of the processor or is loaded therein before being executed. The processor that executes the program code can be the main processor of the EEG monitor or a separate processor.

Figure 4:
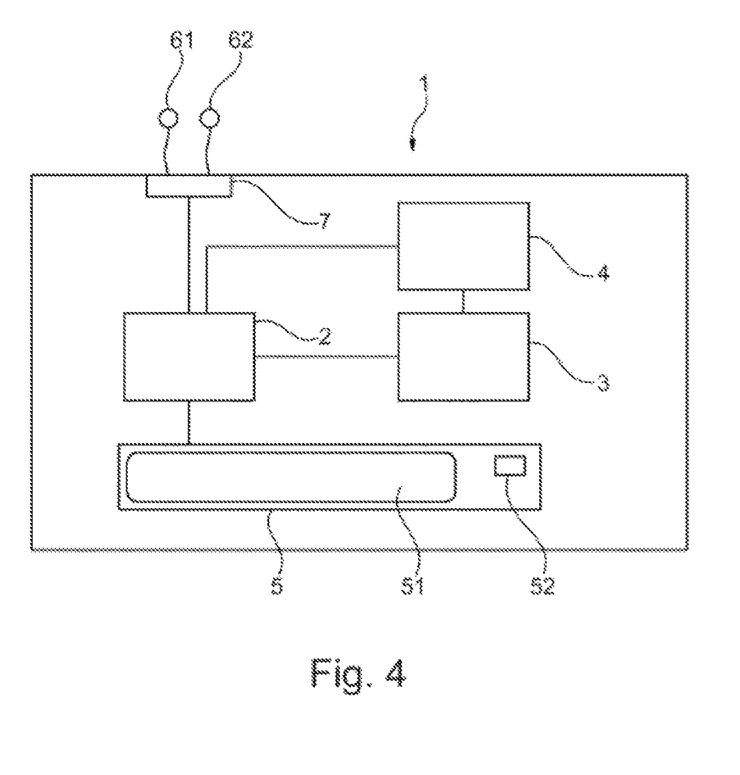
FIG. 4 shows, by way of example, a device for carrying out the method in FIG. 3.

FIG. 4 shows, by way of example, a possible way of implementing such an EEG-based brain function monitor 1. The EEG monitor 1 comprises a microprocessor 2, a memory 3, a control apparatus 4, an output unit 5 and an interface 7 for connecting EEG cables.

By means of the interface 7, EEG cables comprising EEG electrodes 61, 62 can be connected to the EEG monitor 1. Two EEG cables that pick up an EEG signal are depicted by way of example, whereby additional EEG cables can be provided in order to pick up a multichannel EEG signal.

The EEG signal is supplied to the microprocessor 2. The program code is stored in the memory 3 or a program code can be loaded in the memory 3, which, when executed in the microprocessor 2, carries out the method explained with reference to FIG. 3. The process can be controlled by means of the control apparatus 4, and this can be designed to obtain corresponding input commands. The control apparatus 4 can be a main processor of the EEG monitor 1 or can contain such a processor in this case. Alternatively, the functionality of the microprocessor 2 can be taken over by the control unit 4. By means of the control unit 4 and/or additional modules (not shown), additional functionalities of the EEG monitor 1 can be implemented.

When carrying out the loaded program code, the microprocessor 2 therefore determines the absolute minimum of the spectral cutoff frequency and the point in time at which this absolute minimum is present. The corresponding information is transmitted to the output unit 5 and output thereto. This can be done by means of a monitor 51 and/or an acoustic unit 52, for example.

Of course, the invention is not restricted to the above-described embodiments and various modifications and improvements can be made without deviating from the concepts described here. Any of the features can be used separately or in combination with any other features provided that they are not mutually exclusive, and the disclosure extends to, and comprises, all combinations and sub-combinations of one or more features described here. Wherever ranges are defined, these therefore include all the values within these ranges and all sub-ranges that fall within a range.

The invention claimed is:

1. A method for providing a parameter that indicates a loss of consciousness in a patient under anesthetic, wherein the method comprises:
    recording a plurality of electroencephalography (EEG) signals from a head of the patient, wherein the plurality of EEG signals are recorded during a period of time that begins before an anesthesia-inducing medicine is administered to the patient and ends after the loss of consciousness in the patient under anesthetic;
    determining a plurality of spectral cutoff frequencies in the period of time based on the plurality of EEG signals, wherein each of the plurality of spectral cutoff frequencies indicates a frequency within a range of frequencies associated with an EEG signal of the plurality of EEG signals at which a portion of the range of frequencies below the frequency comprises 95% of an overall power of a frequency spectrum associated with the range of frequencies is found;
    determining an absolute minimum associated with the plurality of spectral cutoff frequencies in the period of time, wherein the absolute minimum comprises a lowest spectral cutoff frequency of the plurality of spectral cutoff frequencies in the period of time; and
    providing the parameter that indicates the loss of consciousness in the patient based on the absolute minimum, wherein the parameter is associated with a point in time within the period of time at which the absolute minimum occurs.

2. The method of claim 1, wherein the plurality of EEG signals comprise at least one frontal EEG signal.

3. The method of claim 1, wherein the plurality of EEG signals comprise at least a first EEG signal received from a first electrode and a second EEG signal received from a second electrode at a same time as the first EEG signal, and wherein the at least first and second EEG signals are averaged before a spectral cutoff frequency of the plurality of spectral cutoff frequencies associated with the at least first and second EEG signals is determined.

4. The method of claim 1, wherein the plurality of EEG signals are received using 10-20 system with electrodes that are positioned on the head of the patient in positions F7, F8, Fp1, Fp2 and Fpz.

5. The method of claim 1, wherein the plurality of spectral cutoff frequencies are continuously determined at least every 30 seconds.

6. The method gf claim 1, wherein the parameter is provided as soon as the absolute minimum is determined.

7. The method of claim 1, wherein the parameter is provided when a spectral cutoff frequency of the plurality of spectral cutoff frequencies falls below a value of 10 hertz.

8. The method of claim 1, wherein the absolute minimum is determined when, within the period of time, a subsequently determined spectral cutoff frequency of the plurality of spectral cutoff frequencies is greater than a previously determined spectral cutoff frequency of the plurality of spectral cutoff frequencies.

9. The method of claim 1, wherein a spectral cutoff frequency of the plurality of spectral cutoff frequencies is determined after an EEG signal associated with the spectral cutoff frequency is filtered through a bandpass filter.

10. The method of claim 1, wherein a spectral cutoff frequency of the plurality of spectral cutoff frequencies is determined by spectral analysis of an EEG signal associated with the spectral cutoff frequency.

11. A computer program comprising a program code for carrying out the method according to claim 1 when the computer program is executed on a computer.

12. A device for providing a parameter that indicates a loss of consciousness in a patient under anesthetic, wherein the device comprises:
    one or more sensors to record a plurality of electroencephalography (EEG) signals from a head of the patient, wherein the plurality of EEG signals are recorded during a period of time that begins before an anesthesia-inducing medicine is administered to the patient and ends after the loss of consciousness in the patient under anesthetic; and
    a processor to:
    determine a plurality of spectral cutoff frequencies in the period of time based on the plurality of EEG signals, wherein each of the plurality of spectral cutoff frequencies indicates a frequency within a range of frequencies associated with an EEG signal of the plurality of EEG signals at which a portion of the range of frequencies below the frequency comprises 95% of an overall power of a frequency spectrum associated with the range of frequencies;

determine an absolute minimum associated with the plurality of spectral cutoff frequencies in the period of time, wherein the absolute minimum comprises a lowest spectral cutoff frequency of the plurality of spectral cutoff frequencies in the period of time; and the parameter that indicates the loss of consciousness in the patient based on the absolute minimum, wherein the parameter is associated with a point in time within the period of time at which the absolute minimum occurs.

13. The device of claim 12, wherein the processor continuously determines a spectral cutoff frequency of the plurality of spectral cutoff frequencies at least every 30 seconds.

14. The device of claim 12, wherein the processor provides the parameter as soon as the absolute minimum is determined.

15. The device gf claim 12, wherein the processor provides the parameter when a spectral cutoff frequency of the plurality of spectral cutoff frequencies falls below a value of 10 hertz.

16. The device of claim 12, wherein the processor determines the absolute minimum when within the period of time, a subsequently determined spectral cutoff frequency of the plurality of spectral cutoff frequencies is greater than a previously determined spectral cutoff frequency of the plurality of spectral cutoff frequencies.

17. The device of claim 12, wherein the processor determines a spectral cutoff frequency of the plurality of spectral cutoff frequencies by performing a spectral analysis of an EEG signal associated with the spectral cutoff frequency.

18. The device of claim 12, wherein processor determines a spectral cutoff frequency of the plurality of spectral cutoff frequencies after an EEG signal associated with the spectral cutoff frequency is filtered through a bandpass filter.

19. The device of claim 12, wherein the one or more sensors record at least one frontal EEG signal on the head of the patient, and wherein the plurality of EEG signals comprise the at least one frontal EEG signal.

20. The device of claim 19, wherein the one or more sensors comprise at least a first sensor and a second sensor, and wherein the plurality of EEG signals comprise at least a first EEG signal received from the first sensor and a second EEG signal received from the second sensor, and wherein the processor determines an average of the at least first and second EEG signals before determining a spectral cutoff frequency of the plurality of spectral cutoff frequencies based on the average of the at least first and second EEG signals.

21. An EEG anesthesia monitor comprising a device according to claim 12.

* * * * *